(12) United States Patent
Sebok et al.

(10) Patent No.: US 6,873,411 B2
(45) Date of Patent: Mar. 29, 2005

(54) OPTICAL DEBRIS ANALYSIS FIXTURE

(75) Inventors: Thomas J. Sebok, Tallmadge, OH (US); Joseph P. Kolp, North Canton, OH (US)

(73) Assignee: Lockheed Martin Corporation, Akron, OH (US)

( * ) Notice: Subject to any disclaimer, the term of this patent is extended or adjusted under 35 U.S.C. 154(b) by 729 days.

(21) Appl. No.: 09/923,973

(22) Filed: Aug. 7, 2001

(65) Prior Publication Data

US 2003/0030810 A1 Feb. 13, 2003

(51) Int. Cl.$^7$ .................... G01N 15/02; G01N 21/01; G01N 1/10
(52) U.S. Cl. .................. 356/335; 356/244; 356/246
(58) Field of Search ...................... 356/335, 336, 356/337, 338, 339, 340, 341, 342, 343, 244, 246, 73; 422/100–102

(56) References Cited

U.S. PATENT DOCUMENTS

| | | | |
|---|---|---|---|
| 3,198,064 A | 8/1965 | Moore | 88/14 |
| 3,684,386 A | * 8/1972 | Noll | 356/246 |
| 3,947,121 A | 3/1976 | Cotter et al. | 356/38 |
| 4,393,466 A | 7/1983 | Deindoerfer et al. | 364/415 |
| 4,582,684 A | 4/1986 | Vogel et al. | 422/57 |
| 4,652,095 A | * 3/1987 | Mauro | 359/393 |
| 4,804,267 A | 2/1989 | Greenfield | 356/335 |
| 4,807,267 A | 2/1989 | Rifu et al. | 378/7 |
| 5,030,421 A | 7/1991 | Muller | 422/102 |
| 5,074,662 A | * 12/1991 | Sullivan | 356/244 |
| 5,098,661 A | 3/1992 | Froehlich et al. | 422/102 |
| 5,241,189 A | 8/1993 | Vandagriff et al. | 250/575 |
| 5,594,544 A | 1/1997 | Horiuchi et al. | 356/73 |
| 5,610,712 A | * 3/1997 | Schmitz et al. | 356/335 |
| 5,766,957 A | 6/1998 | Robinson et al. | 436/165 |
| 5,883,721 A | 3/1999 | Gilby et al. | 356/440 |
| 6,104,483 A | 8/2000 | Sebok et al. | 356/244 |

FOREIGN PATENT DOCUMENTS

| | | |
|---|---|---|
| JP | 62-112034 | 5/1987 |
| JP | 7-218417 | 8/1995 |
| WO | WO 95/12118 | 5/1995 |

OTHER PUBLICATIONS

Search Report UK Patent Office dated Sep. 9, 2002.

* cited by examiner

Primary Examiner—Gregory J. Toatley, Jr.
Assistant Examiner—Roy M. Punnoose
(74) Attorney, Agent, or Firm—Renner, Kenner, Greive, Bobak, Taylor & Weber

(57) ABSTRACT

A fixture for imaging particles passing through a cell includes a plate having a plurality of aligned component pin openings and a plurality of mount holes. Several components are mounted to the plate including a camera mount, an illuminator assembly, and a lens support assembly. The camera mount assembly has a pair of registration pins receivable in a pair of plurality of component pin openings, and the camera mount has a pair of base holes alignable with a pair of mount holes for receiving fasteners to secure the camera mount assembly to the plate. The illuminator assembly has a pair of registration pins receivable in a pair of plurality of component pin openings which are in the form of slide slots, the illuminator assembly having a set of flange slots alignable with another pair of the mount holes for receiving fasteners to secure the illuminator assembly to the plate. A pair of nudgers are positioned on opposite sides of the illuminator assembly, wherein each nudger has a rail with a slide slot therethrough, and a head extending from the rail. Each head has an adjuster moveable with respect to the head. The nudger slide slots receiving fasteners to secure the nudger to the plate so that the adjusters can move the illuminator to a desired position prior to securement to the plate.

14 Claims, 7 Drawing Sheets

OPTICAL DEBRIS ANALYSIS FIXTURE

TECHNICAL FIELD

The present invention relates generally to fluid inspection systems. More particularly, the invention relates to a fixture that facilitates precise positioning and alignment of its components to ensure accurate imaging of debris viewed through an optical flow cell carried by the fixture.

BACKGROUND ART

It is known to provide fluid sampling devices using optical near-field imaging as disclosed in U.S. Pat. No. 5,572,320, which is incorporated herein by reference. Such a device is employed to determine the quantity, size, characteristics, and types of particulate matter in fluids. Examples of fluids which are monitored in such a system are lubricating oils used in engines and rotating machinery; hydraulic fluid used in various machinery; and fluids used in industrial quality control, food processing, medical analysis, and environment control. In its most common use, such a device monitors engine oil for metal particulates or flakes, wherein a size, number, and shape of particulates correspond to an engine condition and can alert one to particular problems with the engine. Non-metallic debris in the fluid can also be detected, such as fibers, sand, dirt and rust particles. Predicting failure is critically important in aircraft engines to avoid accidents and loss of life.

The early stages of engine wear cause small particulate matter, of about 50 microns or less in size, to be generated. These particulates have characteristic shapes indicative of the type of wear produced by specific wear mechanisms. As the wear process progresses, the amount and size of particulates increase. Accordingly, imaging and identifying smaller particles allows early identification of faults, thus, allowing more time for corrective maintenance and preventing unexpected catastrophic failures.

The advantage of the aforementioned system over previous systems is readily apparent when one considers that the previous systems only measured the amount of light passing through the material-laden oil, but gave no consideration as to the particular shape of the material. As best seen in FIGS. 1A–G, the various types of images rendered by a known system can provide a clear indication of the types of problems that are likely to occur based upon the shape and structure of the debris monitored. For example, in FIG. 1A, sliding wear particles are shown and these particles are believed to be caused by metal-to-metal contact due to overloading, misalignment, low speed and/or low oil viscosity. The debris shown in FIG. 1B represents fatigue wear particles which are gear or bearing pieces generated due to surface stress factors such as excessive load, contamination, and the like. FIG. 1C shows cutting wear particles that are generated by surface gouging, two body cutting due to break-in, misalignment, and three body cutting due to particle abrasion. FIG. 1D shows oxide particles which are caused by contamination, and red oxide caused by water or insufficient lubrication of the subject machinery.

It will also be appreciated that certain elements may be in the oil that generates false readings. These elements are classified and can be disregarded by the imaging system. For example, as shown in FIG. 1E, fibers are shown which are normally occurring or may be caused by improper sample handling. Instrument problems due to incomplete removal of air bubbles are represented in FIG. 1F. Finally, FIG. 1G shows flow lines which are a result of instrument problems caused by insufficient mixing of a new sample.

In order for such an imaging system to work properly, the system must allow for proper focusing so that the field of view of the fluid to be imaged is within at least plus or minus 20 microns. The debris-containing fluid is pumped through an optical flow cell which is typically held in a fixed position. A laser light illuminates one side of the flow cell and a camera is positioned on the other side. The flow cell is movably positioned to obtain a proper focus. Accordingly, U.S. Pat. No. 6,104,483, which is incorporated herein by reference, facilitates positioning of a flow cell by using a defined reference flange. Although this optical flow cell improves the system's performance, positioning of the other components in the imaging system has been found to be lacking in prior art equipment. In other words, if the other components of the system used to image the fluid passing through the optical flow cell are not properly positioned and aligned, the image obtained by the system may be distorted or, in the worst case, not detected at all.

Previous fixtures employed a camera mounted on a slide device that was incrementally moved until a desired focus was obtained. This position was held in place by tightening screws associated with the slide device. As will be appreciated, tightening the screws slightly adjusts the position of the camera, which may result in the camera being removed from the desired focus. Previous imaging fixtures also required access to both the top and bottom of a plate which supported the slide and other system components. Accordingly, making fine adjustments to the positioning of the camera and the optical flow cell were found to be quite cumbersome and, as a result, performance of routine maintenance on the device was found to be quite difficult. The previous fixture was also problematic in that all of the important components were moveable upon the holding plate and, as such, obtaining a proper focus for the camera was quite difficult. Therefore, there is a need in the art for optical debris analysis fixture which requires minimal adjustment of focus and which allows for simple replacement of the optical flow cell while maintaining focus.

SUMMARY OF THE INVENTION

It is thus an object of the present invention to provide an optical debris analysis fixture.

It is another object of the present invention to provide a fixture that includes a plate which carries a camera mount, a lens support assembly, and an illuminator assembly aligned in a precise manner.

It is a further object of the present invention to provide a fixture, as set forth above, wherein the camera mount and the lens support assembly are positionally fixed upon the plate.

It is yet another object of the present invention to provide a fixture, as set forth above, wherein the illuminator assembly is positionally moveable upon the plate to obtain a proper field of view with respect to the camera mount and the lens support assembly.

It is yet another object of the present invention to provide a fixture, as set forth above, wherein the illuminator assembly is provided with a hinged door to allow for easy and repeatable replacement of an optical flow cell while maintaining the proper focus.

It is still another object of the present invention to provide a fixture, as set forth above, in which a laser light is carried by the plate and directed through the illuminator assembly on a side opposite of the camera mount.

It is still a further object of the present invention to provide a fixture, as set forth above, wherein a pair of nudgers are disposed on opposite sides of the illuminator assembly and wherein the nudgers move the illuminator assembly to a desired position prior to its securement to the plate.

The foregoing and other objects of the present invention, which shall become apparent as the detailed description proceeds, are achieved by an optical debris analysis fixture for obtaining a precise focus for imaging debris passing through an optical flow cell, comprising a plate having a plurality of component pin openings, wherein at least one set of the plurality of component pin openings are plate slots, and a plurality of components detachably mounted to the plate, each of the plurality of components having at least two registration pins that fit into the plurality of component pin openings, wherein one of the plurality of components carries the optical flow cell, and wherein one of the plurality of component's pins are slidably moveable in the slots to allow precise positioning of the one component with respect to the other of the plurality of components.

Other aspects of the present invention are attained by a fixture for imaging particles passing through an optical flow cell, comprising a plate having a plurality of component pin openings and a plurality of mount holes, a camera mount assembly having a pair of registration pins receivable in a first pair of the plurality of component pin openings, the camera mount having a pair of base holes alignable with a first pair of the mount holes for receiving fasteners to secure the camera mount assembly to the plate, and an illuminator assembly having a pair of registration pins receivable in a second pair of the plurality of component pin openings which are in the form of slots, the illuminator assembly having a set of flange slots alignable with a second pair of the mount holes for receiving fasteners to secure the illuminator assembly to the plate.

These and other objects of the present invention, as well as the advantages thereof over existing prior art forms, which will become apparent from the description to follow, are accomplished by the improvements hereinafter described and claimed.

BRIEF DESCRIPTION OF THE DRAWINGS

For a complete understanding of the objects, techniques and structure of the invention, reference should be made to the following detailed description and accompanying drawings, wherein.

BEST MODE FOR CARRYING OUT THE INVENTION

Figure 1A:
FIGS. 1A–G are examples of different types of particles viewed by an optical debris analysis fixture according to the present invention.
Figure 1B:
Figure 1C:
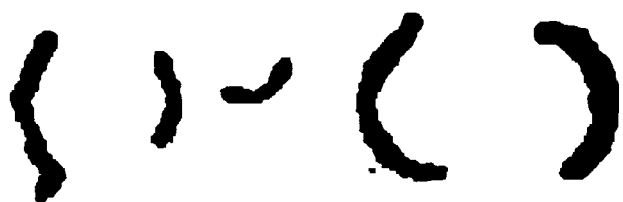
Figure 1D:
Figure 1E:
Figure 1F:
Figure 1G:
Figure 2:
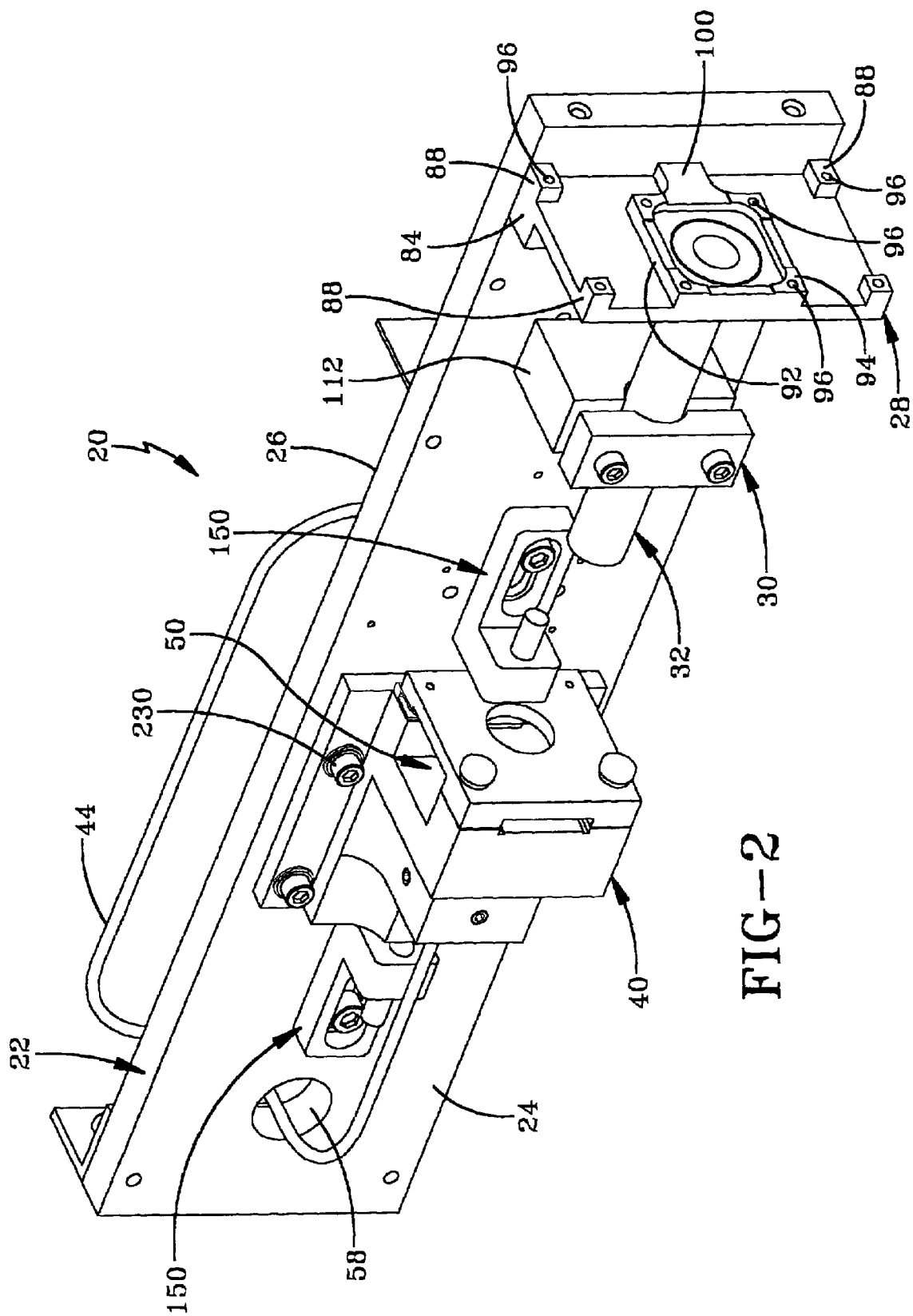
FIG. 2 is a top perspective view of the optical debris analysis fixture according to the present invention.
Figure 3:
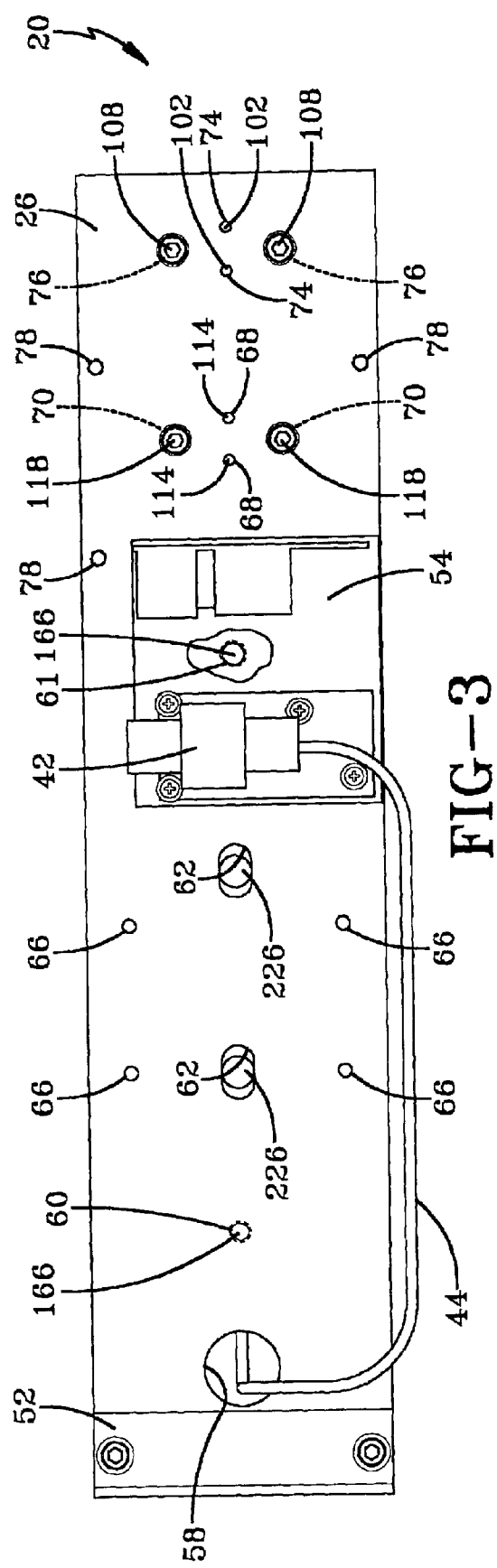
FIG. 3 is a bottom plan view of the fixture.
Figure 4:
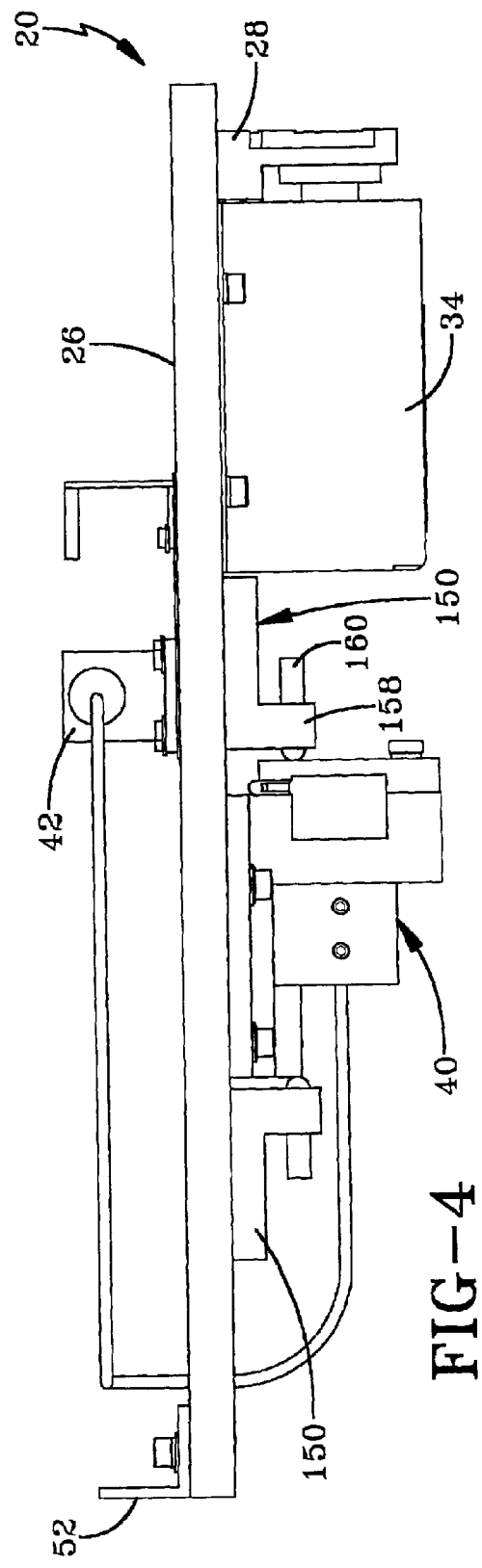
FIG. 4 is an elevational view of the fixture.
Figure 5:
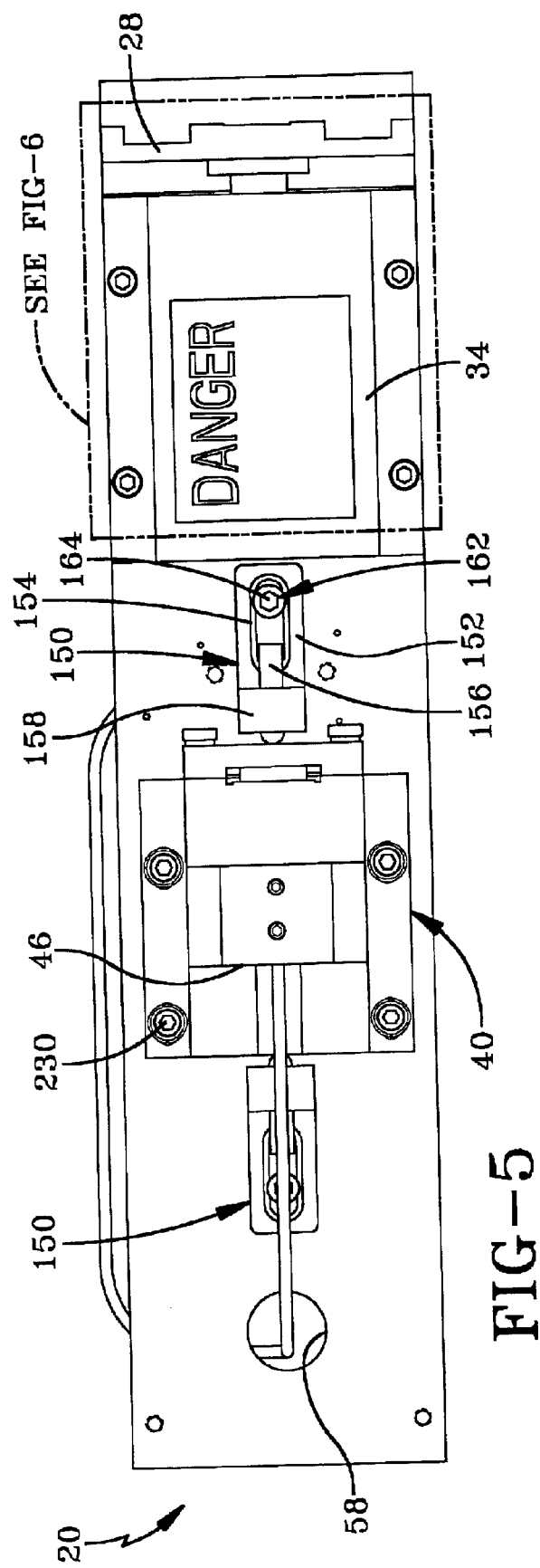
FIG. 5 is a top plan view of the fixture.

Referring now to the drawings and, more particularly to FIGS. 2–6, it can be seen that an optical debris analysis fixture, according to the present invention, is designated generally by the numeral 20. The fixture 20 is carried in a housing (not shown) and associated with other components, which will be discussed in detail below, to image particles contained in a fluid, such as engine oil, to monitor the operational properties of machinery associated with that fluid. The fixture 20 includes a plate 22 which, in the preferred embodiment, is type 430 stainless steel which has a low coefficient of thermal expansion. Of course, any similar material could be used. Such a material is desired so as to maintain the positional relationships of the components which are associated and attached to the plate. The plate 22 has a component side 24 opposite aback side 26. A majority of the components coupled to the fixture 20 are mounted on the component side 24 and they include a camera mount 28, a lens holder assembly 30, a lens 32, a cover 34 which partially encloses the lens 32 and the lens holder assembly 30, and an illuminator assembly 40. A laser 42 is mounted on the back side 26 and generates a laser light that is carried by a fiber optic cable 44 to a collimating lens 46 that is carried by the illuminator assembly 40. The illuminator assembly 40 provides a flow cell cavity 50 for receiving an optical flow cell as described in U.S. Pat. No. 6,104,483, which is incorporated herein by reference. The preferred collimating lens 46 is disclosed in U.S. Pat. No. 5,572,320 and is also incorporated herein by reference. A backside mounting bracket 52 is secured to the back side 26 and is used to secure the fixture 20 in the housing. A middle mount plate 54 is provided for carrying the laser 42 on the plate 22.

Generally, the optical flow cell is carried by the illuminator assembly 40 and connected to a supply of fluid, such as transmission or engine oil, and pumped therethrough. The flow cell is mounted so that the fluid flows vertically downwardly. The laser 42 generates a light that is transmitted through the collimating lens 46 to illuminate the fluid as it flows through the optical flow cell. A camera, not shown, is mounted to the camera mount 28 and images the material to detect particles contained within the fluid. A computer-based processor system (not shown) is connected to the camera for monitoring and processing the detected particles. The processing system contains the necessary hardware, software, and memory to categorize the samples and perform any number of analyses to the particles detected. From this analysis, the user of the fixture 20 may determine whether the machinery associated with the fluid is operating properly and can determine whether a breakdown of the machinery is imminent or if certain parts of the machinery need to be replaced.

The plate 22 has various holes and structural features for precisely positioning the aforementioned components thereon. In particular, the plate 22 includes an optic cable hole 58 that allows for routing the cable 44 from the laser 42 to the illuminator assembly carried on the component side. The plate 22 provides a threaded back nudger hole 60. It will also be appreciated that there is a threaded front nudger hole 61 that is covered by the middle mount plate 54. The plate 22 includes a pair of illuminator slide slots 62 and a set of illuminator mount holes 66, wherein four are preferred in the present embodiment. The plate 22 provides a pair of lens holder pin holes 68 and a set of lens holder mount holes 70. And the plate 22 provides a pair of camera mount pin holes 74 and a set of camera mount holes 76. Also provided are a set of cover mount holes 78. The pin holes and slots 62, 68, and 74 are precisely aligned lengthwise along the plate 22. Each set of pin holes require at least two such that the component received therein or associated therewith does not rotate as it is fastened to the plate 22. Accordingly, more than two pin holes may be associated with each component.

The camera mount 28, which is positioned furthest from the laser light 40, and which is best seen in FIGS. 4–8, includes a base 84. A wall 86 extends upwardly from one side of the base 84 and provides a set of board tabs 88 located in each corner thereof. Each tab 88 provides a threaded hole 90. A camera flange 92 is positioned at about a midsection of the wall 86 and provides a set of four camera tabs 94, each of which has a threaded hole 96. The camera flange 92 has a lens wall hole 98 that extends therethrough. A lens buttress 100 supports the lens wall hole 98. Extending from the bottom of the base 84 are a pair of registration pins 102 and, in particular, one of these pins extends from the bottom of the buttress and one of them extends from the bottom of the base. These registration pins 102 fit in the camera pin holes 74. The base 84 also provides a pair of base holes 106 which align with the camera mount holes 76. The camera mount 28 is positioned upon the plate 22 and fasteners 108 are inserted through the holes 76 and into the holes 106 to securely attach the camera mount 28 to the plate 22. A camera printed circuit board (not shown) is mounted to the tabs 88 and secured to the holes 96 while a camera is secured to the holes 96. The camera, via the printed circuit board, is connected via a Universal Serial Bus to the computer system associated with the fixture as described above.

Figure 6:
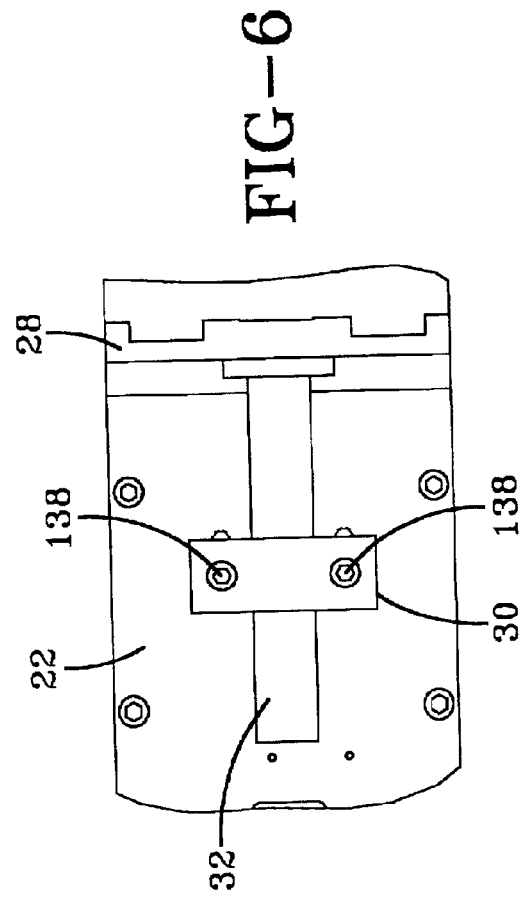
FIG. 6 is a partially broken-away view of a component of the fixture.
Figure 8:
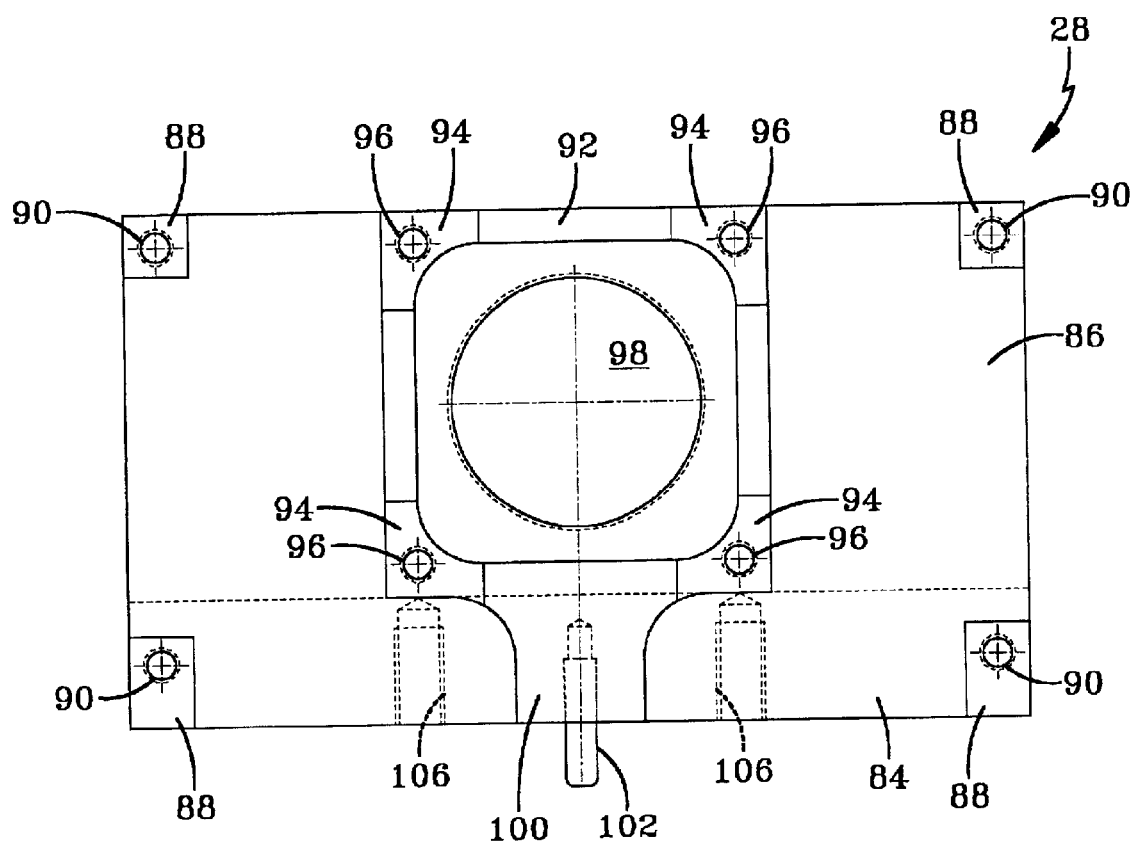
FIG. 8 is an elevational view of the camera mount.
Figure 7:
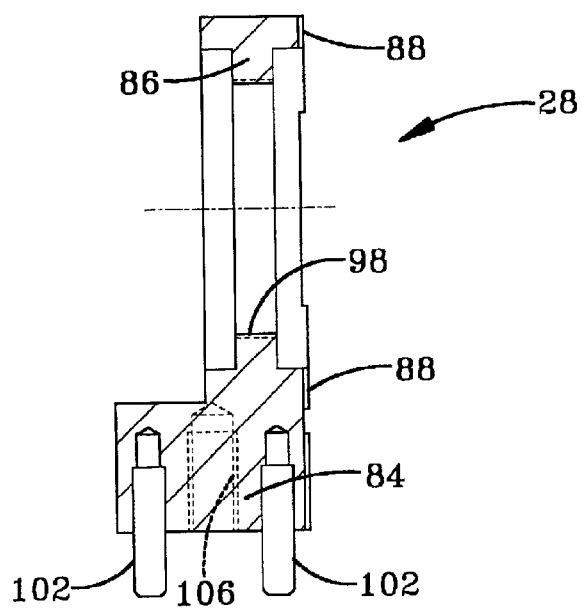
FIG. 7 is a cross-sectional view of a camera mount that is a component of the fixture.
Figure 9:
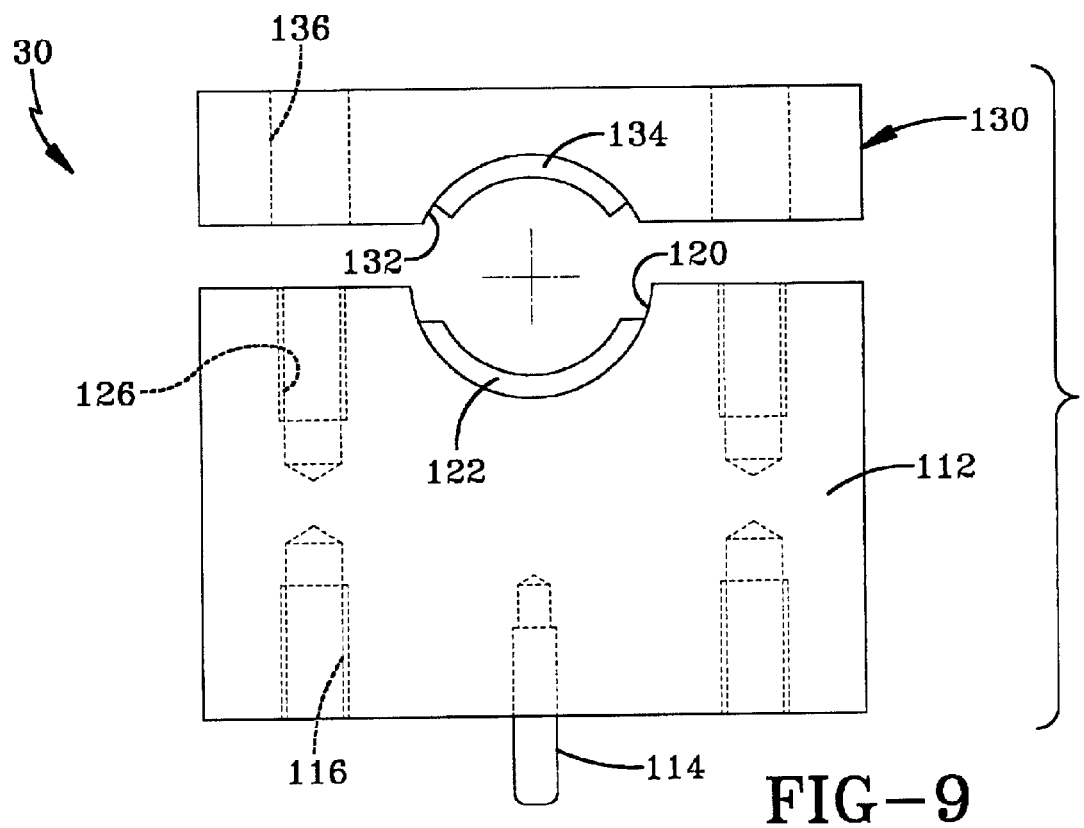
FIG. 9 is an elevational view of a lens support assembly, which is a component of the fixture.

Positioned between the camera mount 28 and the illuminator assembly 40 is the lens holder assembly 30 which is best seen in FIGS. 6 and 9. The lens holder assembly 30 includes a lower block 112. Extending downwardly from the bottom of the lower block 112 are a pair of block registration pins 114 that fit into the pin holes 68. The lower block 112 includes a pair of threaded block holes 116 that are aligned with the mount holes 70 which receive fasteners 118 for securing the lower block 112 to the plate 22. The lower block 112 includes a lower channel 120 which is semi-circular in shape. A rubber or silicon pad 122 may be disposed on the surface of the lower channel 120. A top side of the lower block 112 provides a pair of threaded support holes 126 on either side of the lower channel.

Mateable to the lower block 112 is an upper block 130. The upper block includes an upper channel 132 which is also semi-circular in shape. A pad 134 may be disposed upon the surface of the upper channel 132. The upper block 130 also provides a pair of channel holes 136 that are alignable with the support holes 126. A pair of fasteners 138 are received through the holes 136 and into the holes 126 to clamp the lens 32 when it is received between the lower channel 120 and the upper channel 132. It will be appreciated that one end of the lens 32 is received in the lens wall hole 98.

Referring back to FIGS. 2–5, it can be seen that a pair of nudgers 150 are positioned on opposite sides of the illuminator assembly 40. In particular, one nudger is positioned at a back side of the assembly and the other nudger is positioned between the lens support assembly 30 and a front side of the illuminator assembly 40. Each nudger 150 includes a rail 152 which provides a slide channel 154 through which extends a slide slot 156. Extending upwardly from one end of the rail 152 is a head 158. An adjuster 160 extends through the head 158. The adjuster 160 is moved in a linear direction by rotation in a manner well known in the art. A fastener 162 is received in the slide channel 154 and the slide slot 156. In particular, the fastener 162 has a head 164 from which extends a threaded shaft 166. Each shaft is received within corresponding nudger holes 60 and 61. Accordingly, coarse positioning of the nudgers may be obtained by loosening the fastener 162 and sliding the rail 152 into a desired position. The fastener 162 is then tightened in the appropriate hole 60, 61 such that the head 164 clamps on the slide channel 154. Once the coarse positioning of the nudgers is obtained, the adjusters 160 are moved back and forth to finally position the illuminator assembly 40.

The illuminator assembly 40, which carries the optical flow cell and the collimating lens for the laser light is the only component on the plate 22 which is purposefully moveable until its position is set. All other components on the plate are designed to be immovable once secured. As such, the desired field of view and focus for the camera is obtained by slidably moving the illuminator assembly 40 as provided by the foregoing coacting structures.

Figure 10:
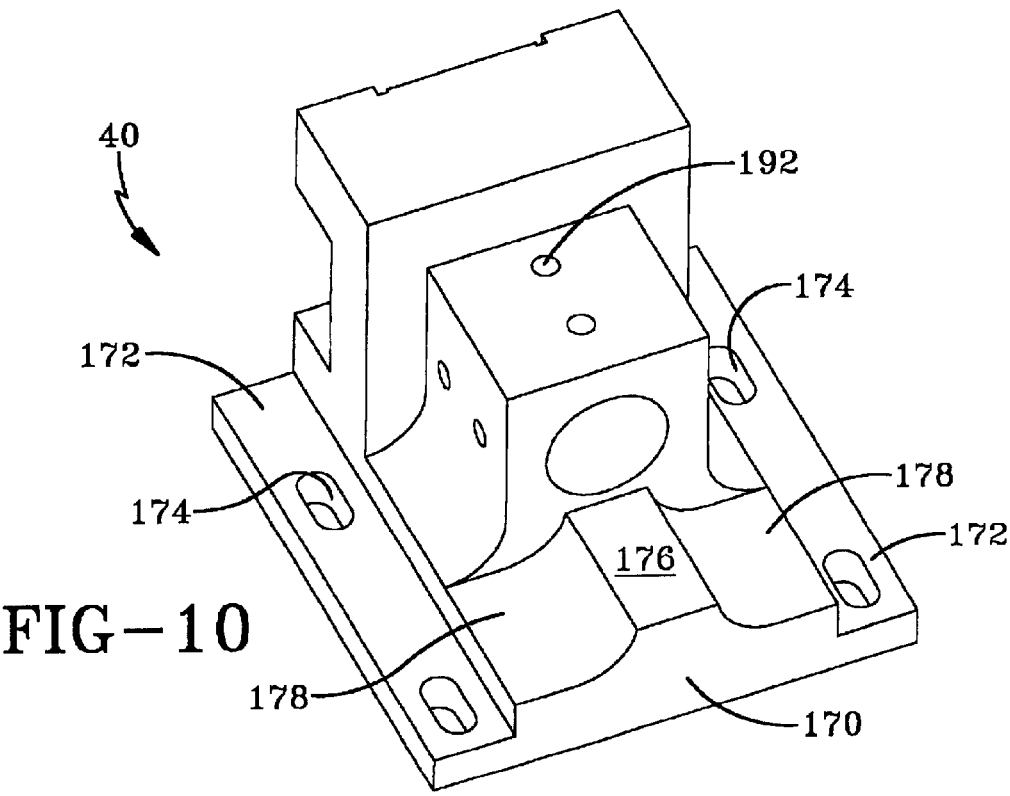
FIG. 10 is a rear perspective view of an illuminator assembly which is a component of the fixture.
Figure 11:
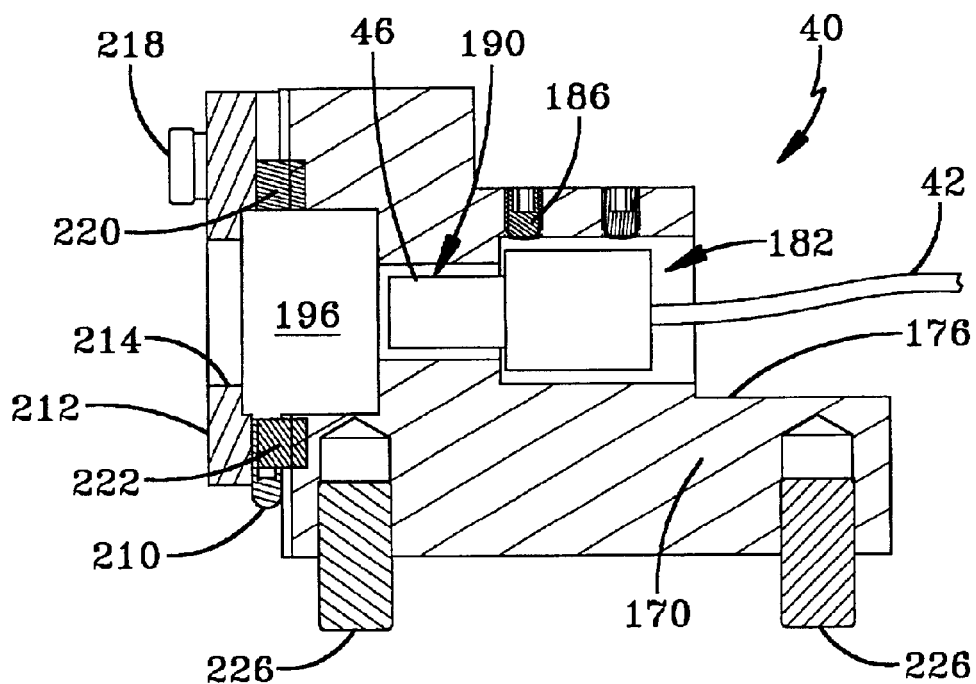
FIG. 11 is a cross-sectional view of the illuminator assembly.
Figure 12:
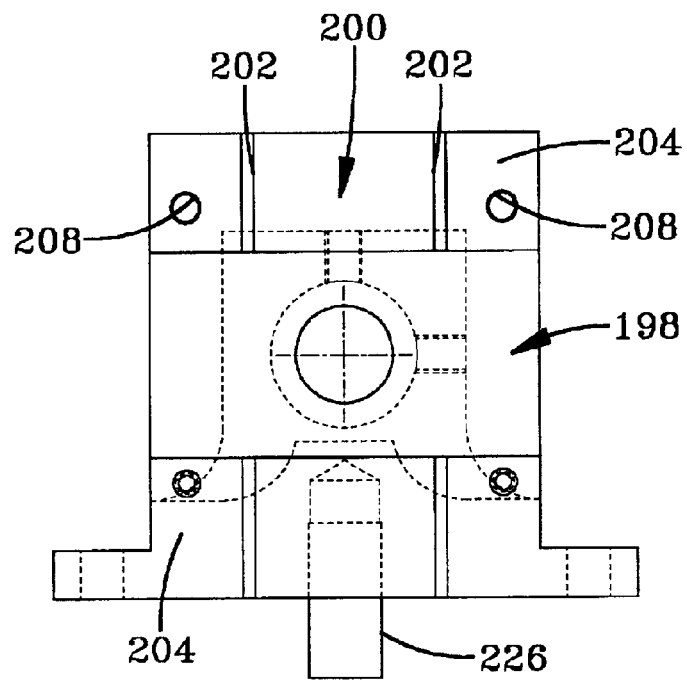
FIG. 12 is an elevational view of the illuminator assembly.

The illuminator assembly 40 includes a block 170 which is best seen in FIGS. 10–12. The block 170 has a pair of laterally extending flanges 172, each of which has a pair of flange slots 174. The block 170 includes a flat cable support 176 with adjacent tapers 178 that extend from the cable support 176 toward the flanges 172. The flat surface 176 supports the fiber optic cable 44 which is terminated into the collimating lens 46. The added mass of the cable support 176 also provides an end surface that is engageable by the nudger 150. The collimating lens and the cable are received in a cable cavity 182 and a lens cavity 190, respectively. The lens cavity 190 provides chamber holes 192. Fasteners 186 are inserted into the chamber holes 192 to hold the lens 46 in place.

The block 170 includes a flow cell chamber 196 for receiving the optical flow cell. In particular, the flow cell chamber 196 provides a housing slot 198 and a flow cell flange slot 200 that is substantially perpendicular in orientation to the housing slot 198. It will be appreciated that the bulk of the housing is received in the housing slot 198 while the reference flanges are received in the flange slots 200. Each side of the flange slot 200 provides a groove 202 that is slightly recessed further into the block 170. It has been determined that any coating or plating of the flange slot produces a rounded corner. By providing the grooves 202, a further recess is provided for this plating such that the positioning of the reference flanges of the optical flow cell is not distorted. In those areas where slots 198 and 200 are not provided, a chamber face 204 is formed. The chamber face 204 provides a set of threaded face holes 208 at the top thereof.

A hinge 210 is connected to the bottom of the chamber face 204 and a door 212 is connected to the other side of the hinge 210. The door 212 provides a door hole 214 that is aligned with the viewing area of the optical flow cell when installed in the illuminator assembly 40. A pair of door fasteners 218 are provided at the side or edge of the door 212 opposite the hinge 210. A top pad 220 and a bottom pad 222 may be provided between or on the door surface that opposes the chamber face 204. Accordingly, when the optical flow cell is installed into the slots 198 and 200, the door 212 is hingedly closed to secure the optical flow cell in place. Once the door 212 is secured by the fasteners 218, the optical flow cell cannot be moved and, as such, it essentially becomes one with the illuminator assembly 40.

Extending downwardly from the bottom of the block 170 are a pair of pins 226 that are slidably received in the illuminator slide slots 62. As such, the illuminator assembly

40 is moveable lengthwise on the plate 22 within those slots to a coarsely defined position. The nudgers 150 are then used to establish the desired image focus. Flange fasteners 230 are received in the flange slots 174 and the illuminator mount holes 66.

A precise position is obtained by moving the adjusters 160 as needed and when it is determined by the software of the computer-based processor system that the image focus of the optical flow cell is set, the fasteners 230 are tightened so as to hold the illuminator assembly 40 in place. This provides a secure reference point for the optical flow cell so that it is always in the proper image focus for the camera mounted to the camera mount 28. This allows for user replacement of flow cells in the field. It is envisioned that all adjustments of the illuminator assembly 40 will be made at the factory prior to shipment.

Advantages of the fixture 20 are readily apparent. In particular, only one element is moved in the assembly so as to maintain the degree of focus of the optical flow cell to plus or minus at least 20 microns. Such a field of view is necessitated so as to properly image the particles contained within the fluid and to provide an accurate analysis of the fluid. It will be appreciated that all of the registration pins of the components are positioned lengthwise along the plate 22 so as to ensure proper side-to-side alignment of the components. Positional alignment is then obtained for the illuminator assembly. Construction of this fixture allows for easy replacement of the optical flow cell by simply loosening the fasteners 218 and removing the optical flow cell from the connecting tubes. A new flow cell may then be inserted and, with the reliable reference point already established in the factory, the door is simply closed and the system is ready for use once again.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. An optical debris analysis fixture for imaging debris passing through an optical flow cell, comprising:
    a plate having a plurality of component pin openings, wherein at least one set of said plurality of component pin openings are plate slots; and
    a plurality of components detachably mounted to said plate, each of said plurality of components having at least two registration pins that fit into said plurality of component pin openings, wherein one of said plurality of components carries the optical flow cell, and wherein one of said plurality of component's pins are slidably moveable in said slots to allow precise positioning of said one component with respect to the other of said plurality of components.

2. The fixture according to claim 1, further comprising:
    a pair of nudgers, said nudgers disposed on opposed sides of said one component, wherein said nudgers are detachably mounted to said plate and wherein said pair of nudgers slidably move said one component to a position within ±20 microns with respect to the other of said components.

3. The fixture according to claim 1, wherein said plurality of components comprise:
    a camera mount for carrying a camera;
    a lens holder assembly for supporting a lens extending from said camera mount; and
    an illuminator assembly which carries the optical flow cell.

4. The fixture according to claim 3, further comprising:
    a pair of nudgers disposed on opposite sides of said illuminator assembly, wherein said nudgers are detachably mounted to said plate and wherein said pair of nudgers slidably move said one component to a position within ±20 microns with respect to at least said camera mount.

5. The fixture according to claim 4, further comprising:
    a light source carded by said plate for directing light through one side of said illuminator assembly and the optical flow cell for observation by the camera carried by said camera mount.

6. The fixture according to claim 5, wherein said illuminator assembly comprises:
    a block;
    a pair of flanges extending from opposite sides of said block, each said flange having a flange slot therethrough;
    a pair of block pins extending downwardly from said block, said block pins receivable in said plate slots, wherein said block is slidable upon said plate by said pair of nudgers and wherein said flange slots receive fasteners that secure said block to said plate when said block is put into position.

7. The fixture according to claim 6, wherein said block has a flow cell housing slot and a flow cell flange slot both of which receive the optical flow cell, said illuminator assembly further comprising:
    a hinged door for detachably securing the optical flow cell in the flow cell housing and flange slots.

8. The fixture according to claim 7, wherein said flow cell flange slot has a groove on both sides thereof.

9. The fixture according to claim 1, wherein said at least two registration pins for each of said plurality of components and said plurality of component pin openings that receive said registration pins are aligned lengthwise along said plate.

10. An optical debris analysis fixture for imaging debris passing through an optical flow cell, comprising:
    a plate having a plurality of component pin openings and a plurality of mount holes;
    a camera mount assembly having a pair of registration pins receivable in a first pair of said plurality of component pin openings, said camera mount having a pair of base holes alignable with a first pair of said mount holes for receiving fasteners to secure said camera mount assembly to said plate; and
    an illuminator assembly having a pair of registration pins receivable in a second pair of said plurality of component pin openings which are in the form of slots, said illuminator assembly having a set of flange slots alignable with a second pair of said mount holes for receiving fasteners to secure said illuminator assembly to said plate.

11. The fixture according to claim 10, further comprising:
    a pair of nudgers positioned on opposite sides of said illuminator assembly, each said nudger having a rail having a slide slot therethrough, and a head extending from said rail, each head having an adjuster moveable with respect to said head, said slide slots receiving fasteners receivable in a third pair of mount hole to secure said nudger to said plate, said adjusters moving said illuminator to a desired position prior to securement of said illuminator assembly to said plate.

12. The fixture according to claim 10, wherein said illuminator assembly has a hinged door that captures the optical flow cell.

13. The fixture according to claim 10, further comprising:

a lens extending from said camera mount.

14. The fixture according to claim 13, further comprising:

a lens holder assembly positioned between said camera mount and said illuminator assembly, said lens holder having a pair of holder registration pins receivable in a third pair of said plurality of component pin openings, said lens holder assembly having a pair of block holes alignable with a fourth set of mount holes for receiving fasteners to secure said lens holder assembly to said plate.

* * * * *